United States Patent
Efthimiadis et al.

(10) Patent No.: US 7,176,034 B2
(45) Date of Patent: Feb. 13, 2007

(54) APPARATUS AND METHOD FOR FILTERING BIOLOGICAL SAMPLES

(75) Inventors: Ann Efthimiadis, Ancaster (CA); Donald McCormack, Stoney Creek (CA)

(73) Assignee: St. Joseph's Healthcare, Hamilton (CA)

( * ) Notice: Subject to any disclaimer, the term of this patent is extended or adjusted under 35 U.S.C. 154(b) by 554 days.

(21) Appl. No.: 10/188,873

(22) Filed: Jul. 3, 2002

(65) Prior Publication Data

US 2004/0005246 A1    Jan. 8, 2004

(51) Int. Cl.
*G01N 1/18* (2006.01)
*C12M 3/06* (2006.01)
*C12M 1/00* (2006.01)
*B01L 3/00* (2006.01)
*B01L 11/00* (2006.01)

(52) U.S. Cl. .................. 436/177; 422/61; 422/99; 422/100; 422/101; 422/103; 435/288.2; 435/288.5

(58) Field of Classification Search .......... 422/99–101, 422/103, 61; 435/288.5, 288.2; 436/177
See application file for complete search history.

(56) References Cited

U.S. PATENT DOCUMENTS

| | | | |
|---|---|---|---|
| 2,110,237 A * | 3/1938 | Parsons | 73/61.71 |
| 2,584,397 A * | 2/1952 | Pitman | 141/59 |
| 2,775,350 A * | 12/1956 | Jones | 210/446 |
| 3,300,051 A * | 1/1967 | Mitchell | 210/339 |
| 3,583,627 A * | 6/1971 | Wilson | 494/36 |
| 3,615,222 A | 10/1971 | Mead | |
| 3,661,265 A | 5/1972 | Greenspan | |
| 3,682,321 A * | 8/1972 | Smith | 210/477 |
| 3,682,596 A * | 8/1972 | Stone | 422/101 |
| 3,701,434 A | 10/1972 | Moore | |
| 3,788,483 A | 1/1974 | Conway | |
| 3,932,277 A | 1/1976 | McDermott et al. | |
| 3,939,822 A | 2/1976 | Markowitz | |
| 3,955,423 A | 5/1976 | Ohringer | |
| 3,969,250 A | 7/1976 | Farr | |
| 3,977,555 A * | 8/1976 | Larson | 215/247 |
| 4,035,294 A | 7/1977 | Landers et al. | |
| 4,131,549 A | 12/1978 | Ferrara | |

(Continued)

FOREIGN PATENT DOCUMENTS

DE    37 22 562 A1    1/1989

(Continued)

*Primary Examiner*—Arlen Soderquist
(74) *Attorney, Agent, or Firm*—Miller Thomson LLP

(57) ABSTRACT

There is provided an apparatus and method for collection and filtration of a sample having a sample holder, a filtrate holder and a connection conduit having a sample receiving end and a filtrate receiving end and containing a filter. The sample holder has an entry end portion and an exit end portion, with a diaphragm normally closing the exit end portion. The filtrate holder has a closeable receiving end portion for receiving the filtered sample. The connection conduit has a rupturing device for rupturing the diaphragm on exit end portion of the sample holder. When the sample holder is inserted into the connection conduit, the diaphragm rupturing device ruptures the diaphragm, allowing the sample be filtered by the filter located within the connection conduit and the filtrate is collected in the filtrate holder. Also described is a method of collecting a biological sample, and filtering the sample, and holding the filtrate in a filtrate holder.

32 Claims, 4 Drawing Sheets

U.S. PATENT DOCUMENTS

| | | | |
|---|---|---|---|
| 4,146,153 A | * 3/1979 | Bailen | 222/83 |
| 4,353,868 A | * 10/1982 | Joslin et al. | 422/101 |
| 4,464,254 A | 8/1984 | Dojki et al. | |
| 4,600,507 A | 7/1986 | Shimizu et al. | |
| 4,678,559 A | 7/1987 | Szabados | |
| 4,783,318 A | * 11/1988 | Lapakko | 422/101 |
| 4,891,134 A | 1/1990 | Vcelka | |
| 5,234,593 A | * 8/1993 | Kuroki et al. | 210/496 |
| 5,322,800 A | 6/1994 | Murphy | |
| 5,393,674 A | * 2/1995 | Levine et al. | 436/177 |
| 5,501,841 A | 3/1996 | Lee et al. | |
| 5,556,544 A | 9/1996 | Didier | |
| 5,582,696 A | * 12/1996 | Sheehan | 204/403.06 |
| 5,603,900 A | * 2/1997 | Clark et al. | 422/101 |
| 5,786,227 A | 7/1998 | Charlton | |
| 5,786,228 A | 7/1998 | Charlton | |
| 5,882,943 A | 3/1999 | Aldeen | |
| 5,976,824 A | * 11/1999 | Gordon | 435/29 |
| 5,981,293 A | 11/1999 | Charlton | |
| 6,210,909 B1 | * 4/2001 | Guirguis | 435/7.2 |
| 6,221,655 B1 | 4/2001 | Fung et al. | |

FOREIGN PATENT DOCUMENTS

| | | | |
|---|---|---|---|
| EP | 350792 | * | 1/1990 |
| WO | WO 01/84113 A1 | | 11/2001 |

* cited by examiner

APPARATUS AND METHOD FOR FILTERING BIOLOGICAL SAMPLES

BACKGROUND OF THE INVENTION

1. Field of the Invention

The present invention relates to a system of retrieving and analysing biological samples that improves the accuracy and reproducibility of results obtained from analysis of mucoid and/or suspension samples. The present invention provides means of promoting standardization of sample collection and analysis between clinical studies and between clinical centres. More particularly, this invention relates to a two vial interconnected filtration system, that allows samples to pass from a sample tube to a filtrate tube, through standardized filters and to be treated with standardized reagents for analysis.

2. Description of the Prior Art

Collection and analysis of biological samples have been valuable for correct diagnosis and therapy of a wide variety of different conditions. In particular, airway inflammation, which is present in many diseases including asthma, chronic obstructive pulmonary disease and lower respiratory tract infections, may be detected from analysis of sputum. Sputum is defined as the expectorated lower respiratory secretions and is composed of fluid and cellular components including eosinophils, neutrophils, lymphocytes, macrophages, and epithelial cells. Analysis of the cells present in sputum is the best, presently known way to characterise the severity and type of inflammation present. This information in conjunction with other clinical parameters may be used to determine specific courses of treatment. Increases in certain types of cells may indicate an infection or an inflammation that would be more sensitive to one course of treatment as opposed to another. Hence, it is important that the collection, processing and analysis of sputum, aspirate, or other biological fluids, are as accurate as possible.

Presently, methodology used for collecting, processing, filtering and analysing biological samples, such as sputum, vary from lab to lab. Variations in technique will cause variations in the results obtained during analysis such as, detection of numbers of cells and fluid phase indices. This becomes important in relation to reproducibility, validity, responsiveness and comparison of results within and between samples. If the results cannot be compared between tests, or if the results of a test cannot be reproduced, valid diagnosis and accurate courses of treatment cannot be determined. Procedures and the equipment used must therefore be standardised.

An important part of the process for analysis of certain biological samples, is the filtration of the collected sample and the collection of the filtrate containing the single cell or cellular suspension that the technician wishes to analyse. Variation in the protocol for processing samples for analysis is currently one area that causes variation in results between tests and between testing centres. The variation in results is largely due to of the wide variability in protocols, reagents, and materials currently used for the collection and analysis of samples.

When dealing with limited quantities of samples for analysis, even a minute loss of sample could drastically alter the results of a test. The size, number and type of cells found in the filtrate vary depending on the size and type of filter used. Incorrect filter pore size may result in selective cell loss and incorrect cell differentials. Incorrect filter mesh type and size may result in cell loss due to absorption of small samples. Improper placement of the filter may allow the filtrate to become contaminated by debris. Contaminates or debris may cause problems in analysis by varying the results that are produced, or by clogging apertures of automated cell counters. In addition to this, each time that a sample is handled and transferred from one vessel to another there will be loss of sample volume and content causing errors in the analysis and the final results of the experiment. Selection of the filter type and size necessary for removal of undesirable contaminants and debris is an important component that contributes to reproducible and valid results.

There is a need for a system that will standardize the protocol used by various technicians and labs so that results may be cross-referenced and prepared for diagnostic purposes between samples, between tests and between laboratories. Reasons for comparing test results between samples would be, for example, if a patient is being treated by a certain type of drug it is desirable to know if the prescribed drug is having an effect on the condition present.

Samples may be collected at various points during a course of treatment and comparison of measurements such as cell counts and/or fluid phase indices may be analysed to determine effect of treatment. Clinical treatment may then be adjusted accordingly. Lack of standardized tests complicate comparison of analysis results of different samples, which may make it impossible to make an absolute clinical diagnostic decision, and to monitor treatment. It would not be definitive if variations in results were due to erroneous procedures or to actual change as a result of treatment. A system developed with a standardized collection and filtration procedure could eliminate many errors in the handling, examination and measurement of a sample. A system in which a sample could be collected in a sample holder, transported to the lab and then filtered through an internal filtration conduit into a second receiving vial, would be a desirable contribution to science. Currently, in most cases, samples are being collected in one collection vessel or sample holder. The sample is then transported to a lab. The sample is then poured from this vessel onto filters of varying sizes depending on the protocol in use. The filtered sample, or filtrate, is then received in a second receiving vessel, or filtrate holder. Transfers of a sample from vessel to vessel many times will cause loss of volume and cell yield.

In accordance with the invention disclosed herein, it will be seen that a device is used for collecting a sample, filtering the sample through a filter with a standardized mesh size, and receiving the filtered sample directly into another connected vessel. A device capable of performing these steps in a closed system will provide a solution to many of the aforementioned problems. The steps of collection, filtration, collection of filtrate and analysis, could be conducted within one system and would eliminate transfer of sample. This may reduce chances of sample volume being lost, wrong filter sizes or types being used or improper filter positioning, thus preventing debris from passing through into the filtrate causing contamination. This system will use a standardized filter type and pore size, or have various filters available within a kit for specific purposes. The collected samples could be treated with reagents, in the collection vial or sample holder if desired. Treating the sample in the collection vial may therefore eliminates transfer steps and reduces sample loss. Use of a standardised system having standard filters, reagents, and apparatuses, would therefore allow all technicians to use the same protocol and result in comparable data and thus be reproducible and valid.

Furthermore, a system that eliminates or greatly reduces human exposure to the sample is greatly desirable in settings where that sample may contain contagions. In accordance with the present invention, the collection or sample holder may be sealed from human contact from the point of collection. Both the receiving or collection vials may have reagents placed in it prior to collection or processing.

A device that could reduce the number of errors in processing a sample, increase the validity, reproducibility and simplify a process would be of great interest to pharmaceutical companies, hospitals, and research laboratories. There could be a decrease in the number of man-hours necessary and a reduction in the amount of reagents and equipment used for analysis, therefore a reduction in costs.

Availability of a standard filtering system along with various standardized filters, and testing reagents in a kit would provide a standardized protocol and be an advantage for producing valid and reproducible result The foregoing and other objects and advantages of the present invention will become more apparent from the following summary and the detailed description of the present invention, when taken in conjunction with the accompanying drawings, the scope of which will be pointed out in the appended claims.

SUMMARY OF THE INVENTION

In accordance with this invention, there is provided an apparatus for collection of a mucoid or suspension sample for filtration which comprises a sample holder, a filtrate holder, and a connection conduit containing a filter, which can be connected between the sample and filtrate holders. The suspension sample passes from the sample holder through the filter, which collects contaminants such as debris, and passes to the filtrate holder as filtrate. The sample holder has an entry end portion for collecting the mucoid or suspension sample, and an exit end portion. A diaphragm, or a valve, or a perforated disc mechanism seals the exit end. When the sample holder is connected with the connection conduit, a diaphragm rupturing device then ruptures the diaphragm of the sample holder, thus allowing the suspension sample to flow freely from the sample holder to the filter that is contained within the connection conduit. The suspension sample passes through the filter, purifying the sample by removal of contaminates such as debris. The filtrate is then received in the filtrate holder, which may be removed, sealed and taken to a lab for analysis and processes demanded by the tests that are being performed. The sample and filtrate holders of the filtration system may be inscribed with graduated markings for easy determination of the volume of sample contained therein, thus allowing direct calculation of concentration.

The diaphragm rupturing device, as illustrated in the preferred embodiment, is a male shaped protrusion. The diaphragm of the sample holder is aligned with the male shaped protrusion such that the diaphragm rests on top of the male shaped protrusion. The male shaped protrusion ruptures the diaphragm of the exit end portion of the sample holder when the sample holder and the rupturing device are pushed together, thus forcing the protrusion to puncture the diaphragm. As illustrated by the preferred embodiment, the diaphragm rupturing device is mounted on a support member, which is mounted within the connection conduit. When the sample holder is connected to the connection conduit, and pressure is applied, the diaphragm is forced against the male shaped protrusion. As the support member moves closer relative to the connection conduit, in the direction of the applied force, the diaphragm is moved to one side, permitting the sample to flow into the connection conduit. Although the support member is illustrated in the preferred embodiment as fixed in the connection conduit, in another embodiment it could be a mounted on a moveable support member.

The male shaped protrusion defines a pathway or conduit through which the suspension sample flows from the sample holder. The pathway is a hollow channel through the male shaped protrusion, and connects the sample holder to an interior chamber in the connection conduit, located between the diaphragm rupturing device and the filter, within the connection conduit. The diaphragm rupturing device could be a variety of members that could cause a rupture or tear in a diaphragm, and is not limited to a male shaped protrusion. The suspension sample could flow directly from the ruptured diaphragm into the connection conduit without the aid of a channel, if desired.

It should be noted that the use of a diaphragm and a rupturing device is only one method for connecting the sample holder to the filter and the filtrate holder. Other possible means of connection may include a selfsealing elastomeric end, through which a syringe type connector may be inserted, such as the type used for drug vials. Another embodiment may use perforated rotatable disks, such that the perforations on each disk will allow a sample to flow through only when the perforations are aligned with one another. When the perforations are not aligned with one another, the perforations are sealed by the opposing disk.

The connection conduit may also support an inlet, which passes from the outside of the connection conduit to the interior chamber of the connection conduit. The inlet allows introduction of solutions from outside the filtration system. This would be desirable, to allow introduction of filter wetting solutions, and reagents or the like, without opening the filtration system to the environment, thus preventing risk of spillage, contamination of the sample, or exposure of the technician to infectious agents.

The interior chamber is defined by the walls of the connection conduit, the diaphragm rupturing device and support member, and a filter. Once the diaphragm is ruptured, the suspension sample flows from the sample holder, through the male shaped protrusion channel, into the interior chamber and onto the filter, where it is filtered and collected in the filtrate holder.

DESCRIPTION OF THE INVENTION

Figure 1:
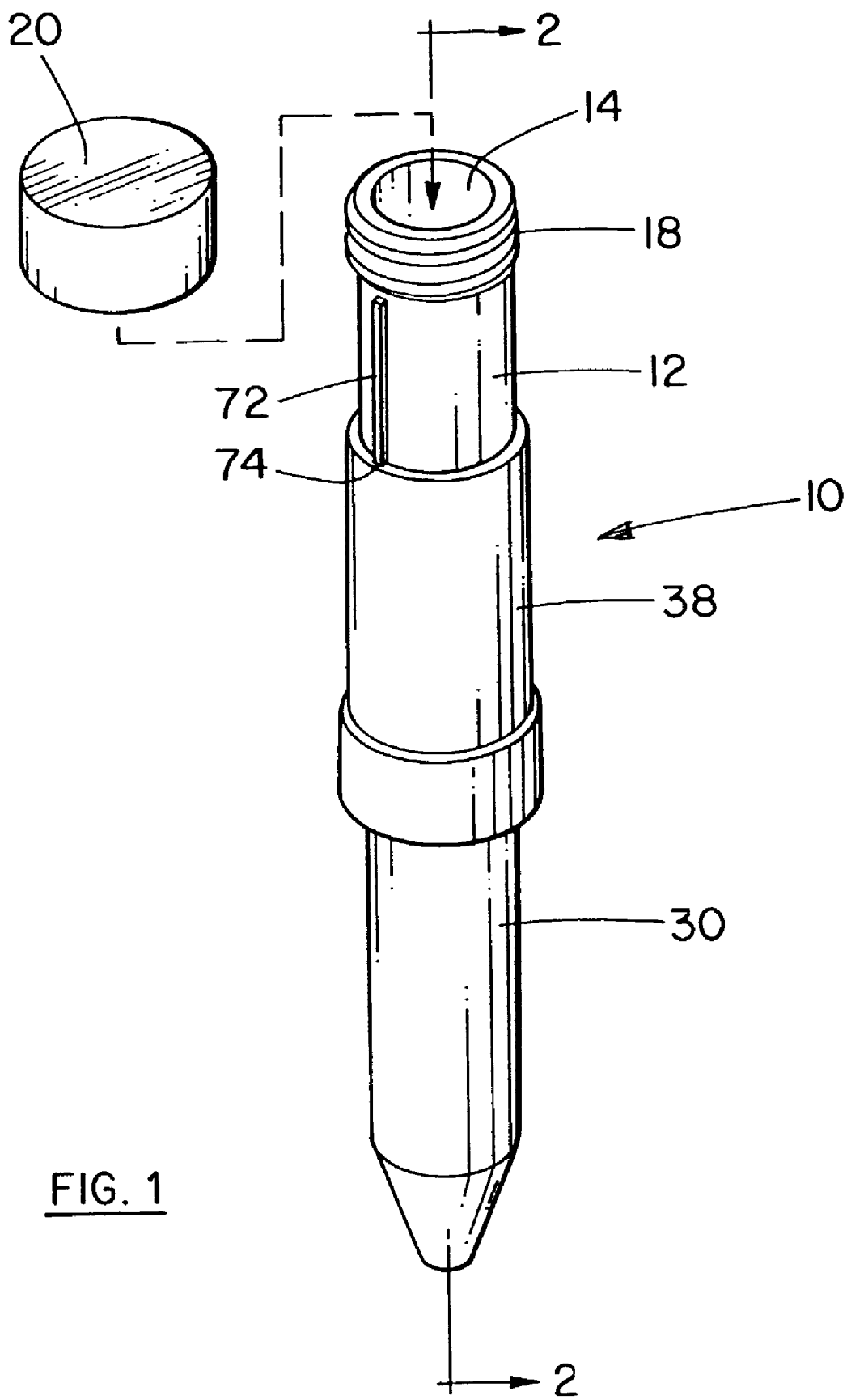
FIG. 1 is a perspective illustration of the sample collection device partially exploded.

The invention is illustrated in a preferred embodiment, in the form of a device in which sputum aspirate or other biological suspension samples may be sampled in a three part sampling and filtration system (10), as illustrated in FIGS. 1 through 9. The filtration system (10) includes a collection or sample holder (12).

The collection or sample holder (12) for collection of a biological sample, such as a mucoid or suspension sample, has an entry end portion (14) and an exit end portion (16). The entry end portion (14) for collecting a suspension sample is closeable and has outer threads (18) allowing cap, stopper, or other closure (20) with attachments such as inner threads (not shown) to be attached to the entry end portion (14) in a well known manner. The exit end portion (16) of the sample holder (12) defines an opening (22) which is temporarily closed, for example in this case, being rupturably sealed with diaphragm (24). The diaphragm (24), typically made of a prophylactic material of a type that is unreactive with the suspension sample collected for filtration, seals the exit end portion (16) and retains the collected sample in the sample holder (12). The sample holder (12) is inscribed with graduated markings,(not shown) for easy determination of sample volume.

Around the diaphragm (24), a sloping ledge (26) is formed inside exit end (16), for reasons to be described below. Diaphragm (24) is mounted on a hinge flap (28), and is normally bonded to ledge (26), (FIG. 2), until engaged by the rupture device, described below.

The receiving or filtrate holder (30) of the illustrated embodiment, is generally made of the same material as the sample holder (12), and is closed at one end, in this case the lower end, as illustrated. The filtrate holder (30) has an open ended receiving end portion (32) with attachments such as outer threads (34), and is closeable after collection of the filtrate with a cap, stopper, or other closure (36) which may have interior threads (not shown). The filtrate holder (30) may also be inscribed with graduated markings for easy determination of volume of filtrate received.

The connection conduit (38) of the illustrated embodiment, has a sample receiving end portion (40) for connection with the exit end portion (16) of the sample holder (12). In this embodiment, the sample holder (12) has a circumference at its exit portion (16), which is smaller than the interior circumference of the sample receiving end portion (40) of the connection conduit (38). This permits the exit end (16) of sample holder (12), to make a telescopic sliding fit into the receiving end (40) of connection conduit (38). However other configurations are possible. The connection conduit (38) has a lower attachment end (42), which is threaded on its interior and is adapted to be attached to the open or receiving end (32) of filtrate holder 30.

The connection conduit (38), in this embodiment, is shaped to receive a diaphragm rupturing device (44) on support member (46). The diaphragm rupturing device (44) defines a pathway (48) through which the suspension sample will flow, from the sample holder (12) after the diaphragm (14) on the exit end portion (16) of the sample holder (12) is ruptured. Vacuum release hole (50) passes through wall (52) of the connection conduit (38). Vacuum release hole (50) allows equalization of pressure, which thereby permits the sample to flow after diaphragm (24) is ruptured.

The above described connection between the sample holder (12) and filtrate holder (30) and the connection conduit (38), illustrate only one method of connection. It should be noted that the method of connection is not restricted to the telescopic sliding fit described. Other forms on interconnection are possible.

The diaphragm rupturing device (44), as illustrated in the preferred embodiment, (FIGS. 5 and 9), is a male shaped tubular protrusion (54). This is formed by defining an angled edge (56), at the free end of protrusion (54).

The male shaped protrusion (54) ruptures the diaphragm (24) of the exit end portion (16) of the sample holder (12) when pressure is applied, forcing the sample holder (12) into the connection conduit (38). As the sample holder (12) slides into connection conduit (38), edge (56) of male shaped protrusion (54) presses against and ruptures the diaphragm (24), thereby swinging the diaphragm 24 inwardly (FIG. 8) about its hinge flap 28, to one side of sample holder (12).

Alternatively, it will be appreciated that the rupture device (44) could be mounted on some form of slide (not shown), which would be manually slidable relative to connection conduit (38). In this case when the sample holder (12) was connected to the connection conduit (38), pressure would be applied on the diaphragm (24) by a male shaped protrusion (54) which is moved relative to the axis of connection conduit (38).

The male shaped tubular protrusion (54) defines a pathway or channel (58) through which the suspension sample flows from the sample holder (12), into connection conduit (38). The pathway (58) extends through the male shaped protrusion (54), and connects the sample holder (12) to connection conduit (38).

Within connection conduit (38) there is also received a filter support (60). Filter support (60) is cylindrical in exterior shape and makes a snug pressure fit within the attachment end (42) of connection conduit (38). Filter support (60) defines an interior filter support wall (62) of generally frusto-conical shape in section, wider at its upper end and tapering to its lower end. A drainage tube (64) extends downwardly from its lower end. Connection conduit (38) defines at its lower end a flange (66), which functions to retain filter support (60) in position within connection conduit (38).

Figure 9:
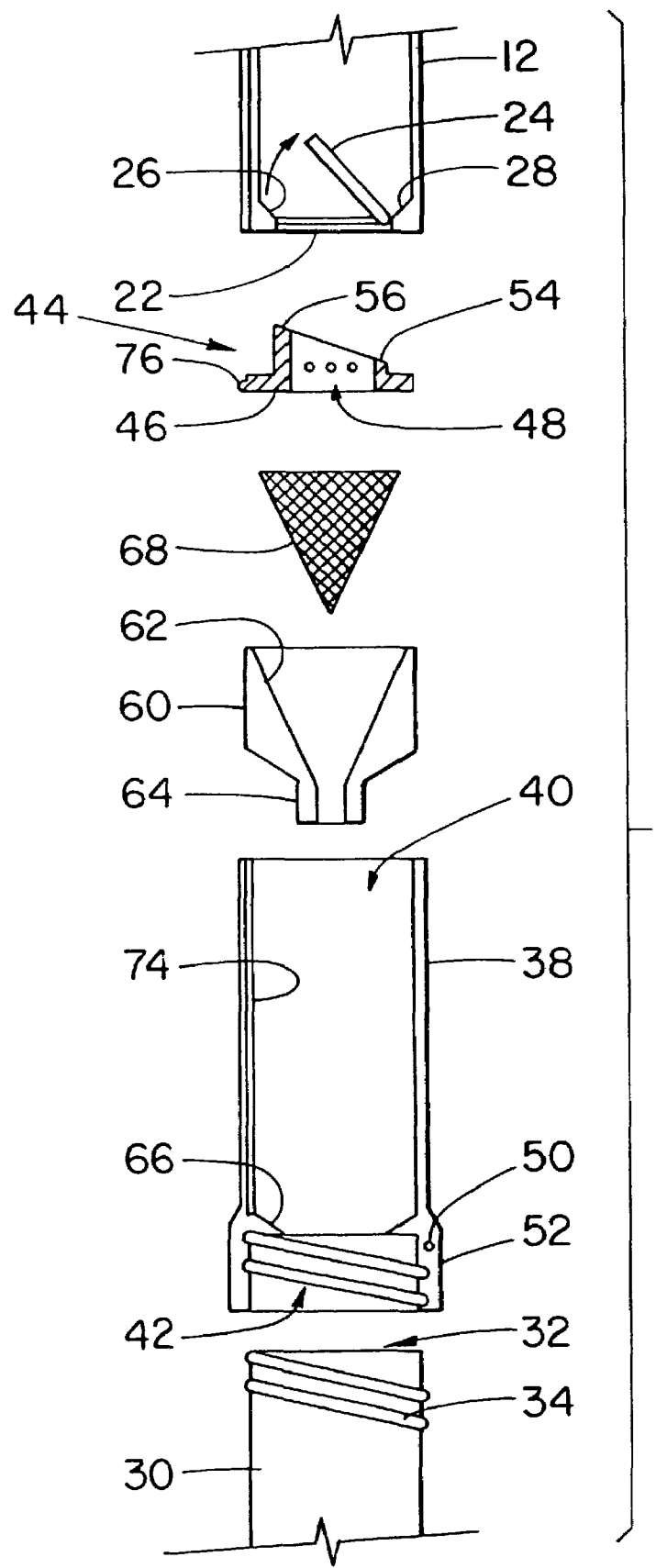

A filter media (68) made of suitable, preferably disposable, filter material, is located within filter support (60). It is of conical shape, in this embodiment, and is supported by filter support wall (62) (FIG. 9). The invention is not restricted to any particular shapes however. Filters, and filter supports could be of any functional shape. The filters could simply be flat discs in some cases, resting on any suitable frame work (not shown) allowing flow of filtrate from the filter.

Free flow of sample liquid from sample holder (12), down though filter media (68) is permitted by allowing entry of air through air vent hole (50) provided in wall (52) of connection conduit (38).

In order to ensure complete drainage of sample liquid from sample holder (12) a plurality of drain holes (70) are provided around male tubular protrusion (54). These ensure that any liquid which might collect around the outside of male protrusion (54), can drain through such holes (70) and flow down through the filter media (68).

The air inlet (50), which passes from the outside of the connection conduit (38) to the interior also allows introduction of solutions from outside the filtration system. This would be desirable, to allow introduction of filter wetting solutions, reagents or the like, without opening the sample collection system (10) to the environment. This will prevent risk of spillage, contamination of the sample or exposure of the technician to infectious agents.

In order to ensure that the sample holder (12) and the connection conduit (38) are guided into the correct relation during telescopic interconnection, sample holder (12) is formed with an exterior guide ridge (72), and connection conduit (38) is formed with a complementary guide groove (74). When these two are registered and in sliding relation, the sample holder will be guided into the correct rotational orientation relative to the connection conduit (38), to ensure easy rupture of the diaphragm (24)

Similarly, the support (46) of the rupture device (44) has a guide block (76) formed thereon, and guide block (76) also fits into guide groove (74) of connection conduit (38). This ensures that the rupture device (44) is in a preset orientation, when pressed into connection conduit (38), which corresponds with the desired orientation of sample holder (12).

Many methods may be used for capping and sealing the filtrate holder (30), such as a threaded cap, stopper, or other closure for example.

In Operation

Figure 2:
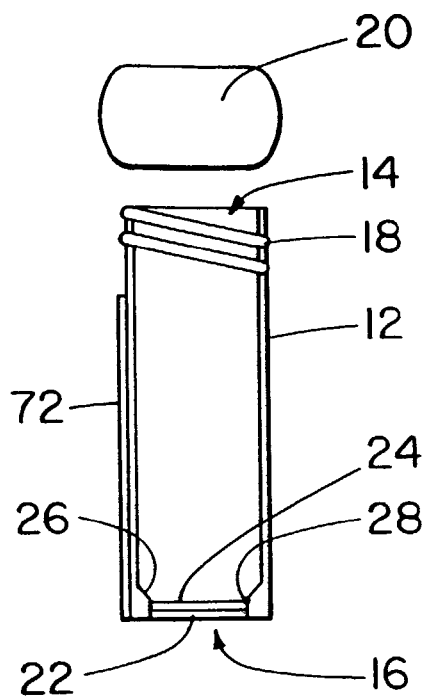
FIG. 2 is a vertical section of a first component, the sample holder, of the sample collection device.

In operation a physician, technician, nurse, or the like, collects a biological sample or a series of samples in a series of sample holders (12), from the subject source or different subject sources, into the entry end portion (14) of the sample holder (12). At this time the exit end portion (16) of the sample holder (12) is still sealed by the rupturable diaphragm (24) and may be covered by a protective means (not shown) to prevent accidental rupture of the diaphragm (24). The entry end portion (14) of the sample holder (12) is then capped or sealed by a sealing means, such as cap, stopper, or other closure (20) and the sample holder (12) is transported for testing (As shown in FIG. 2). If desirable, reagents may be added to the collected sample in the sample holder (12).

At the testing facility, the exit end portion (16) of the sample holder (12) is attached to the sample receiving end portion (40) of the connection conduit (38) by threads or some other convenient connection means. In the case of this embodiment, the sample holder (12) is then slid into the connection conduit (38) and gradually pressed further into telescopic engagement. This will bring male protrusion (54) into contact with diaphragm (24)(See FIGS. 6 and 7).

At a suitable point in the operation, a solution may be introduced through the hole (50), in this embodiment by means of injection, or may be introduced through a resealable injection port (not shown) of a type well known in the art, for wetting the filter and/or mixing with the sample before filtration.

Figure 3:
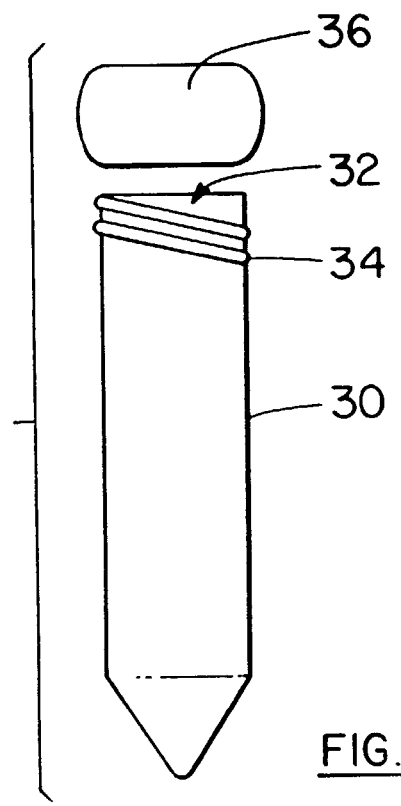
FIG. 3 is a vertical section of a second component, the filtrate holder, of the sample collection device.
Figure 4:
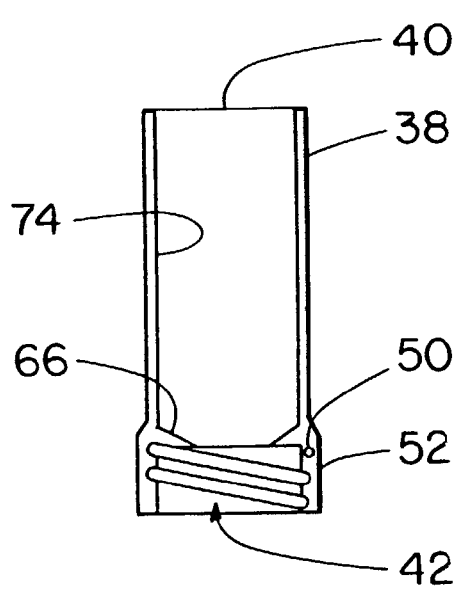
FIG. 4 is a vertical section of a third component, the connection conduit, of the sample collection device.
Figure 5:
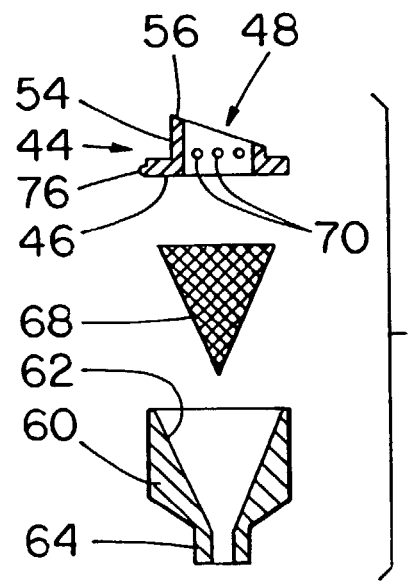
FIG. 5 is a exploded vertical side elevation of the three filter components of the sample collection device.
Figure 6:
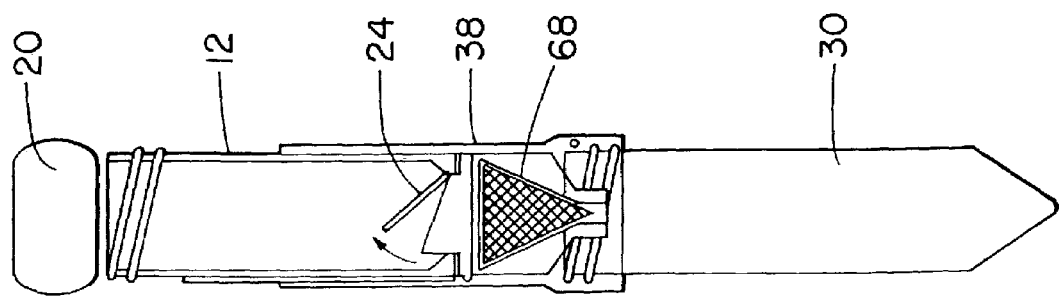
FIG. 6 is a vertical section of some components of the sample holder, shown partially assembled, at a first assembly stage.
Figure 7:
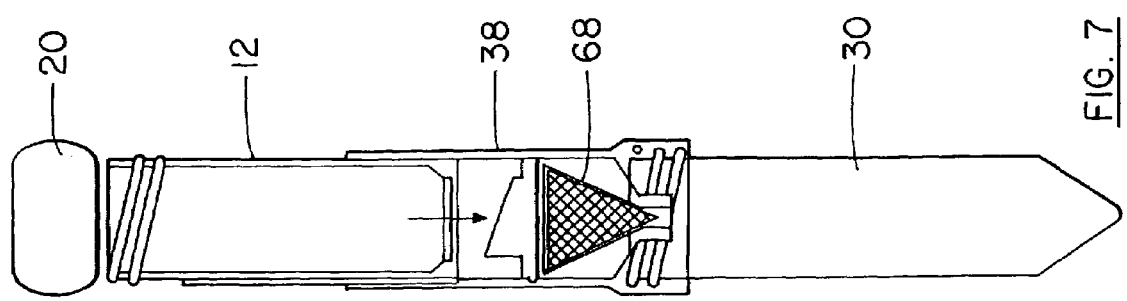
FIG. 7 is a vertical section corresponding to FIG. 6 of all the components showing the collector vial partially inserted into the connection conduit, at a second assembly stage.
Figure 8:
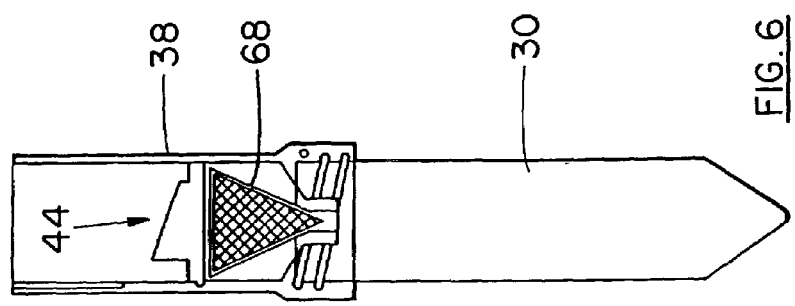
FIG. 8 is a vertical section corresponding to FIG. 7 showing the collection vial fully inserted into the connection conduit, at a third assembly stage; and, FIG. 9 is an exploded side elevation of the three filter components and portions of the sample holder, the connector conduit and the filtrate holder.

Further relative movement between sample holder (12) and connection conduit (38) will rupture diaphragm (24) (FIG. 8). Once the diaphragm (24) is ruptured, the sample flows from the sample holder (12), through the male shaped tubular protrusion (54), and flows into the connection conduit (38), and onto the filter media (68). There it is filtered and drains though drain tube (64) and flows into the filtrate holder (30). The filtrate holder (30), as illustrated in this embodiment, will already have been attached to the connection conduit (38) by threads (34). When filtration is complete, the filtrate holder (30) may then be removed from the connection conduit (38) and capped, or otherwise closed, and sealed for storage, transport or for testing procedures such as cell counts and centrifugation (FIG. 3).

In this embodiment, as the sample passes through the filter media (68), any debris or contaminates that are larger than the pores (not shown) or mesh size (not shown) of the filter media (68) are removed.

The sample holder (12) and the connection conduit (38), together with entire filter assembly and filter media (68) may be discarded, or the parts may be sterilized for future use with a replacement filter.

Once the filtrate is received in the filtrate holder (30), a closeable cap, stopper, or other closure (not shown), or other form of seal, protects the purified sample or filtrate from becoming contaminated, or lost due to spillage, and also protects technicians and the like from exposure. The closure may be removed when testing of the purified sample begins. After use, the filtrate holder (30) may be sterilized for future use or discarded.

Typically the entire system can be supplied in kit form. A sterile pack (not shown) would contain the sample holder (12), the connection conduit (38), containing the filter support (60), filter media (68) and rupture device (44) already locked in place, and a filtrate holder (30), and suitable cap, stopper, or other closures or other seals, and dosage sized containers of reagents, filter wetting fluids and the like, and possibly gloves for handling the entire system, and a face mask. Such a kit, in pack form, would ensure that as far as possible all samples were taken in the same manner, and were all handled under sterile conditions, and were all filtered to the same degree.

The foregoing is a description of a preferred embodiment of the invention which is given here by way of example only. The invention is not to be taken as limited to any of the specific features as described, but comprehends all such variations thereof as come within the scope of the appended claims.

What is claimed is:

1. An apparatus for collection of a suspension sample for filtration comprising:
a sample holder for collecting the suspension sample, said sample holder having an entry end portion, an exit end portion, and a rupturable separating means at said exit end portion;
a filtrate holder for receiving the suspension sample;
a connection conduit having a sample holder connection end for connecting to said sample holder, said connection conduit having a filtrate holder connection end for connecting to said filtrate holder, thereby connecting said sample holder to said filtrate holder and a rupturing device for rupturing said rupturable separating means at said exit end portion of said sample holder, thereby allowing the suspension sample to exit said sample holder; and
a filter mounted in said connection conduit, whereby the suspension sample passes through said filter before entering said filtrate holder.

2. The apparatus as claimed in claim 1, wherein said rupturable separating means at said exit end portion of said sample holder is a diaphragm normally closing said exit end portion.

3. The apparatus as claimed in claim 2, wherein said entry end portion of said sample holder is closeable.

4. The apparatus as claimed in claim 3, wherein said rupturing device for rupturing said diaphragm is a male shaped protrusion, said male shaped protrusion defining a pathway through which the suspension sample exits said sample holder.

5. The apparatus as claimed in claim 4, wherein said male shaped protrusion is tubular and is formed with an angled edge.

6. The apparatus as claimed in claim 5, wherein said connection conduit has a filter support mounted therein.

7. The apparatus as claimed in claim 6, wherein said filtrate holder has a receiving end portion for receiving the filtered suspension sample from said connection conduit.

8. The apparatus as claimed in claim 7, wherein said filtrate holder is closeable at said receiving end portion, after reception of said filtrate.

9. The apparatus as claimed in claim 6, further comprising a filter media supported by said filter support.

10. The apparatus as claimed in claim 9, wherein said filter media is conical, and wherein said filter holder defines a generally frusto-conical support wall and a drainage tube at the apex thereof.

11. The apparatus as claimed in claim 10, wherein said diaphragm is hingedly mounted to said sample holder.

12. The apparatus as claimed in claim 11, further comprising an angled ledge formed around the interior of said sample holder for receiving said diaphragm.

13. The apparatus as claimed in claim 12, wherein said support member is formed with connection guides and wherein said connection conduit is formed with mating guides to guide relative movement there between.

14. A method of filtering a suspension sample, comprising the steps of:
    collecting a sample in a sample holder, said sample holder having an exit end portion sealed by a closure;
    connecting a filtrate holder to said sample holder;
    opening said closure;
    allowing the suspension sample to flow from said sample holder to a filter and filtering the suspension sample through said filter; and
    collecting said filtered sample in said filtrate holder.

15. The method of filtering a suspension sample as claimed in claim 14, further comprising the step of collecting the suspension sample at an entry end portion of said sample holder.

16. The method of filtering a suspension sample as claimed in claim 15, further comprising the step of closing said entry end portion of said sample holder.

17. The method of filtering a suspension sample as claimed in claim 16, further comprising the step of connecting said sample holder to a sample receiving end portion of said connection conduit.

18. The method of filtering a suspension sample as claimed in claim 17, further comprising the step of passing a solution through an inlet, whereby said filter is moistened.

19. The method of filtering a suspension sample as claimed in claim 18, further comprising the step of sealing said inlet, thereby preventing loss of the suspension sample.

20. The method of filtering a suspension sample as claimed in claim 19, further comprising the step of rupturing said diaphragm on a male shaped protrusion of said connection conduit.

21. The method of filtering a suspension sample as claimed in claim 20, further comprising the step of closing said filtrate holder by a closing device.

22. A connection apparatus for connecting a sample holder and a filtrate holder, comprising:
    a connection conduit having a sample holder connection end for connecting said sample holder, said connection conduit having a filtrate holder connection end for connecting said filtrate holder, to connect said sample holder to said filtrate holder;
    a filter mounted in said connection conduit, whereby a suspension sample must pass through said filter when passing from said sample holder to said filtrate holder; and
    a rupturing means a male shaped protrusion mounted to a support member, said support member is moveably mounted on said connection conduit and is adapted to engage the sample holder connection end.

23. The connection apparatus as claimed in claim 22, further comprising an inlet in said connection conduit at said filtrate holder connection end, wherein said inlet defines an opening into said connection conduit through which a solution may be passed.

24. The connection apparatus as claimed in claim 23, wherein said inlet is resealable by a removable stopper.

25. A method of filtering a liquid sample for analysis using a sample holder having an entry end portion and an exit end portion, said exit end portion rupturably sealed, a connection conduit having a sample holder connection end portion and a filtrate holder connection end portion, and a filtrate holder having a receiving end portion, comprising the steps of:
    collecting the sample through said entry end portion of said sample holder; attaching said exit end portion of said sample holder to said sample holder connection end portion of said connection conduit;
    attaching said receiving end portion of said filtrate holder to said filtrate holder connection end portion of said connection conduit;
    rupturing a rupturable seal of said exit end portion of said sample holder, on a male shaped protrusion mounted within said connection conduit;
    allowing the sample to flow from said exit end portion of said sample holder through a filter located within said connection conduit;
    allowing the filtered sample to exit said connection conduit;
    allowing the filtered sample to enter said receiving end portion of said filtrate holder; and
    removing said filtrate holder from said connection conduit.

26. An apparatus for collection of a suspension sample for filtration comprising:
    a sample holder for collecting a sample, wherein said sample holder has a entry end portion and an exit end portion, said entry end portion of said sample holder being closeable and said exit end portion of said sample holder having a diaphragm normally closing said exit end portion and being rupturable to release said sample;
    a filtrate holder for receiving said sample, wherein said filtrate holder has a receiving end portion for receiving said sample, and wherein said filtrate holder is closeable at said receiving end portion;
    a connection conduit, wherein said connection conduit has a sample holder connection end for connection to said sample holder and a filtrate holder connection end for connection to said filtrate holder, thereby connecting said sample holder to said filtrate holder;
    a support member mounted in said connection conduit;
    a rupturing device connected to a support member, said rupturing device for rupturing said diaphragm of said exit end portion of said sample holder, wherein said rupturing device for rupturing said diaphragm is a male shaped protrusion, said male shaped protrusion defining a pathway through which the suspension sample exits said sample holder; and
    a filter mounted in said connection conduit, whereby the sample must pass through said filter before entering said filtrate holder.

27. The apparatus as claimed in claim 26, wherein said connection conduit has an inlet, said inlet defining an opening though which a solution may pass.

28. The apparatus as claimed in claim 27, wherein said support member is moveably mounted in said connection conduit.

29. The apparatus as claimed in claim 26, wherein said exit end portion of said sample holder is closeable whereby said diaphragm is protected from rupture.

30. The apparatus as claimed in claim 27, wherein said inlet is resealable.

31. The apparatus as claimed in claim 30, wherein said sample holder and said filtrate holder have graduated markings inscribed thereon for direct measurement of sample volume.

32. A filtering system kit comprising:
- at least one sample holder for collecting a sample, wherein said sample holder has an entry end portion and an exit end portion, said entry end portion of said sample holder being closeable and said exit end portion of said sample holder having a diaphragm normally closing said exit end portion and being rupturable to release said sample;
- at least one filtrate holder for receiving said sample, wherein said filtrate holder has a receiving end portion for receiving said sample, and wherein said filtrate holder is closeable at said receiving end portion;
- at least one connection conduit, wherein said connection conduit has a sample holder connection end for connection to said sample holder and a filtrate holder connection end for connection to said filtrate holder, thereby connecting said sample holder to said filtrate holder;
- a rupturing device in said connection conduit, said rupturing device for rupturing said diaphragm of said exit end portion of said sample holder, wherein said rupturing device for rupturing said diaphragm is a male shaped protrusion, said male shaped protrusion defining a pathway through which said sample exits said sample holder;
- at least one filter mountable in said connection conduit, whereby said sample must pass through said filter before entering said filtrate holder;
- at least one closure for closing said at least one sample holder and filtrate holder; and
- at least one reagent for use in said filtering system.

* * * * *